United States Patent [19]

Turnbull

[11] Patent Number: 5,201,310

[45] Date of Patent: Apr. 13, 1993

[54] MEDICO-SURGICAL TUBE WITH SEALING CUFF AND A SUCTION LUMEN AT THE TOP OF THE CUFF

[75] Inventor: Christopher S. Turnbull, Hythe, England

[73] Assignee: Smiths Industries Public Limited Company, London, England

[21] Appl. No.: 792,626

[22] Filed: Nov. 15, 1991

[30] Foreign Application Priority Data

Dec. 5, 1990 [GB] United Kingdom ............... 9026405

[51] Int. Cl.⁵ ................. A61M 16/00; A61M 29/00
[52] U.S. Cl. .................... 128/207.15; 128/207.14; 604/96; 604/102
[58] Field of Search ............. 128/207.14, 207.15, 128/911, 912; 604/102, 96, 103, 118, 119, 128

[56] References Cited

U.S. PATENT DOCUMENTS

| | | | |
|---|---|---|---|
| 1,598,283 | 8/1926 | Kinney | 604/96 |
| 2,892,458 | 6/1959 | Auzin | 604/96 |
| 3,762,125 | 8/1988 | Leiman et al. | 128/207.15 |
| 4,305,392 | 12/1981 | Chester | 128/207.15 |
| 4,327,721 | 5/1982 | Goedin | 128/207.15 |
| 4,584,998 | 4/1986 | McGrail | 604/102 |
| 4,607,635 | 8/1986 | Heyden | 128/207.15 |
| 4,632,108 | 12/1986 | Geil | 128/207.15 |
| 4,637,389 | 1/1987 | Heyden | 128/207.15 |
| 4,834,087 | 5/1989 | Coleman et al. | 128/207.14 |
| 4,840,173 | 6/1989 | Porter, III | 128/911 |
| 5,067,497 | 11/1991 | Greear et al. | 128/207.15 |

FOREIGN PATENT DOCUMENTS 3406294 9/1985 Fed. Rep. of Germany.

Primary Examiner—Edgar S. Burr
Assistant Examiner—K. L. Asher
Attorney, Agent, or Firm—Pollock, VandeSande and Priddy

[57] ABSTRACT

A cuffed tracheal tube has a suction lumen extending along the tube and opening through a suction aperture immediately adjacent the upper, proximal end of the cuff. The inflatable cuff is attached to the external surface of the tube by collars. The proximal collar is everted within the inflatable portion of the cuff so that it does not extend beyond the inflatable portion and so that the maximum amount of secretions can be removed through the suction aperture.

4 Claims, 2 Drawing Sheets

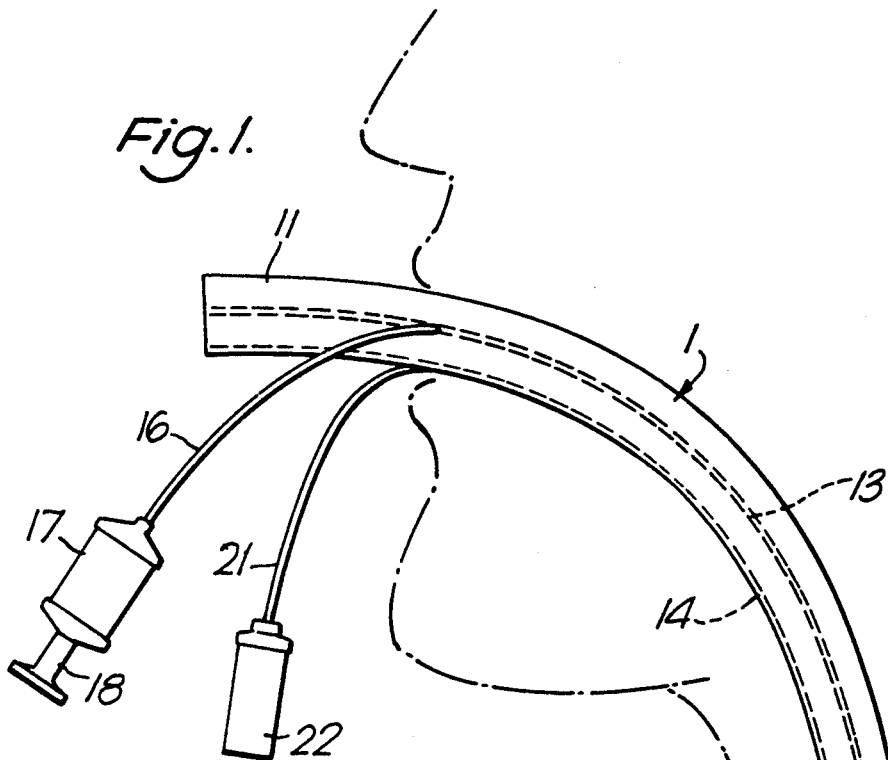
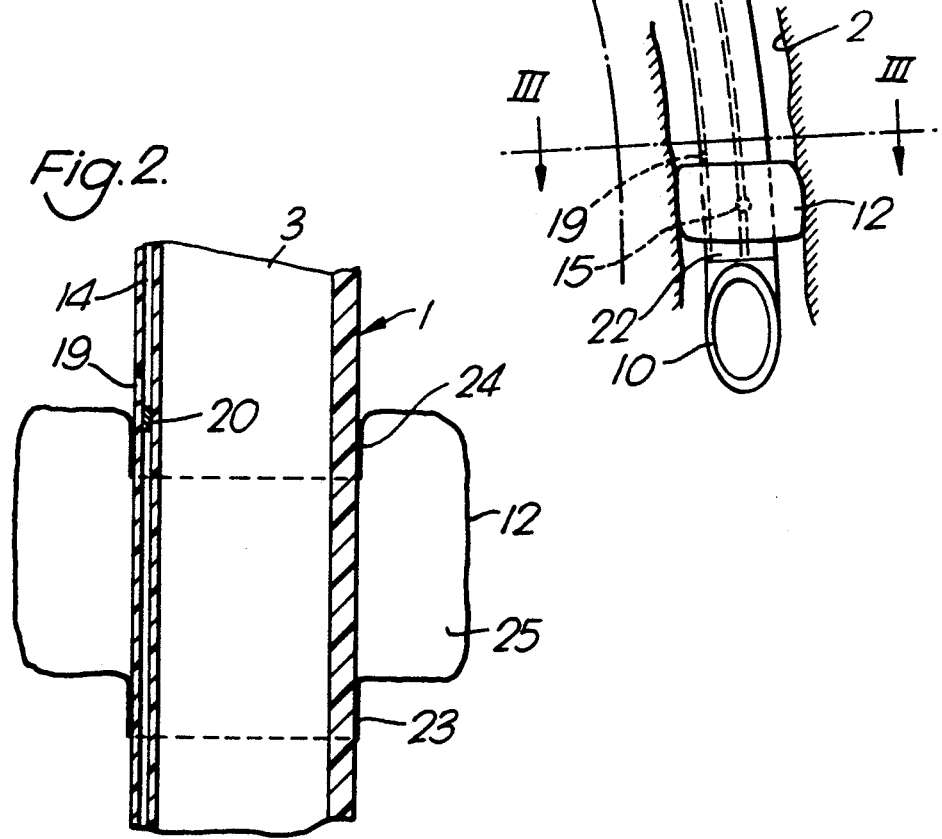

MEDICO-SURGICAL TUBE WITH SEALING CUFF AND A SUCTION LUMEN AT THE TOP OF THE CUFF

BACKGROUND OF THE INVENTION

This invention relates to medico-surgical tubes and assemblies.

The invention is more particularly concerned with cuffed medico-surgical tubes, such as, for example, cuffed tracheal tubes in which an inflatable cuff seals the tube with a patient's trachea.

Such cuffed tubes can present a problem in that secretions produced above the cuff in the trachea, or other body channel in which the tube is located, will be prevented from flowing along the channel and will thereby collect above the cuff, providing a site for the accumulation of bacteria and infection.

Various proposals have been made previously for removing such secretions by providing a suction aperture above the cuff. In Heyden U.S. Pat. No. 4,607,635 there is described a tracheal tube having a channel which opens at various locations along its length and through which a suction catheter can be inserted to remove secretions at any desired location above the cuff. In Chester U.S. Pat. No. 4,305,392 there is described a tracheal tube with a bulbous chamber above the cuff in which secretions are collected for removal through a suction lumen extending through the wall of the tube. The problem with both of these tubes is that it is not possible to remove secretions that collect immediately above the cuff. This is because the cuff is conventionally attached to the wall of the tube by means of short collars at opposite ends of the cuff, which are adhered to the tube and extend above and below the cuff. The length of the collar above the cuff defines the closest distance by which the suction aperture can be spaced from the cuff, because any attempt to form a suction aperture through the collar would weaken the join of the cuff to the tube and possibly lead to leakage from the cuff. In Porter U.S. 4,840,173 there is suggested a way in which secretions close to the cuff could be removed, by providing a suction tube which projects over the proximal collar of the cuff. This, however, would have the disadvantage of being relatively complex and expensive to make and provides an undesirable projection from the side of the tube which could irritate the delicate surface of the trachea. There is also the risk that the end of the suction tube may damage the cuff or become blocked by the cuff. This risk can be reduced by making the upper end of the cuff more rigid, but this is a further complication in the construction of the tube.

BRIEF SUMMARY OF THE INVENTION

It is an object of the present invention to provide a medico-surgical tube which can be used to avoid the above-mentioned disadvantages.

According to one aspect of the present invention there is provided a medico-surgical tube having a cuff embracing the tube with an inflatable portion of the cuff adapted to seal the outside of the tube with the wall of a body cavity within which the tube is inserted, the cuff being attached to the tube by respective collar portions at opposite ends of the cuff, a suction lumen extending along the tube to the region of the proximal end of the cuff, a suction aperture opening from the lumen to the exterior of the tube immediately adjacent the proximal end of the cuff, the proximal end of the cuff being folded back so that a part at least of the inflatable portion of the cuff overlies the proximal collar portion so that the proximal collar portion does not extend beyond the inflatable portion of the cuff.

The suction lumen preferably extends along the tube within the wall thickness of the tube. The external surface of the proximal collar portion is preferably attached to the tube. The internal surface of the distal collar portion may be attached to the tube. The cuff may be adapted to seal with the trachea and the suction lumen be adapted to remove secretions that collect in the trachea above the cuff.

An endotracheal tube, in accordance with the present invention, will now be described, by way of example, with reference to the accompanying drawings.

BRIEF DESCRIPTION OF THE DRAWINGS

FIG. 1 is a side elevation view of the tube;

FIG. 2 is an enlarged cross sectional view of a part of the tube;

DESCRIPTION OF THE PREFERRED EMBODIMENTS

Figure 3:
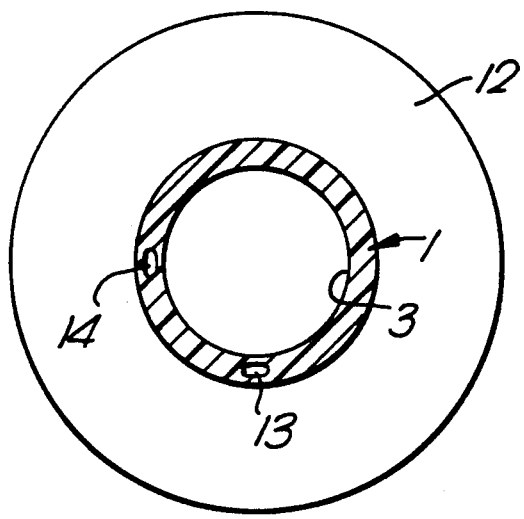
FIG. 3 is an enlarged transverse section along the line III—III of FIG. 1.

With reference first to FIGS. 1 to 3 there is shown an endotracheal tube assembly 1 with its distal, patient end 10 in trachea 2 of a patient and with its proximal, machine end 11 projecting from the patient's mouth. An inflatable cuff 12 encompasses the outside of the tube close to its patient end 10 and serves to seal the tube with the trachea. The tube 1 has a primary lumen 3 which opens at both ends of the tube and provides a gas passage for ventilation of the patient's lungs.

The tube 1 is of a semi-flexible plastics material and may be made by a conventional extrusion process with two secondary lumens 13 and 14 extending axially along the tube within the wall thickness. Both lumens 13 and 14 are closed at the two ends of the tube such as by heat sealing or by plugs inserted into the lumens.

One of the secondary lumens 13 provides a passage for inflation and deflation of the cuff 12 and opens through the outside wall of the tube 1 via an aperture 15 which opens into the interior of the cuff. The inflation lumen 13 is sealed below the aperture 15. Close to the machine end of the tube, a small-diameter inflation line 16 has one end joined in the inflation lumen 13 to that the inflation lumen continues through the inflation line. At the other end of the inflation line 16, there is provided a and conventional inflation indicator 17 and coupling 18 by which a syringe (not shown) can be connected to supply air, via the inflation lumen 13, to inflate the cuff 12.

The other secondary lumen 14 is a suction lumen which opens close to its distal end through a suction aperture 19 in the outside wall of the tube 1 located immediately adjacent the cuff 12. The suction lumen 14 is closed on the distal side of the suction aperture 19 such as by a plug 20 inserted in the lumen 14. Close to the proximal, machine end of the tube 1, a small-diameter suction line 21 has one end joined into the suction lumen 14 so that the suction lumen continues through the suction line. At its other end, the suction line 21 has a coupling 22 by which connection can be made to a suction pump and collection vessel (not shown).

The cuff 12 is attached to the outside wall of the tube 1 in a manner different from that in conventional tubes. The cuff 12 is a thin-walled blow moulding of PVC or a similar plastic and is of tubular shape and circular section having two collar portions 23 and 24 at opposite ends. The internal diameter of the collar portions 23 and 24 is the same as the external diameter of the tube 1. Between the two collars 23 and 24, over the major part of its length, the cuff 12 has a diameter which is greater than that of the tube 1 so that, when assembled on the tube, this forms an inflatable portion 25 of the cuff which has a substantially constant diameter along its entire length, when inflated within the trachea. The distal, patient end collar 23 is joined to the tube in the conventional manner so that it extends beyond the inflatable portion 25 and has its internal surface bonded to the external surface of the tube 1, such as by means of a solvent. The opposite, proximal or machine end collar 24 is joined in a different manner by everting it, so that it is folded inside the inflatable portion 25 and is bonded to the tube 1 by what was originally the outside surface of the collar. In this way, the inflatable portion 25 of the cuff 12 overlies the proximal collar 24 of the cuff. It can be seen that this enables the suction aperture 19 to be located immediately adjacent the inflatable portion 25 of the cuff 12 so that any secretions from the upper part of the trachea which collect above the cuff can be removed by suction through the aperture 19 with very little secretions, if any, remaining above the cuff.

The tube 1 is inserted in the trachea in the usual way, with the cuff 12 deflated. When correctly positioned, the cuff 12 is inflated by means of a syringe connected to the inflation line coupling 18 with a measured amount of air, so as to inflate the cuff to the desired pressure and produce an effective seal with the trachea. Ventilation can then be carried out by connecting the tube 1, at its machne end, to a conventional ventilation/anaesthetic machine. Periodically, a suction pump or similar device, such as a syringe, is connected to the coupling 22 of the suction line 21, to remove secretions that have collected in the trachea above the cuff 12.

Figure 4:
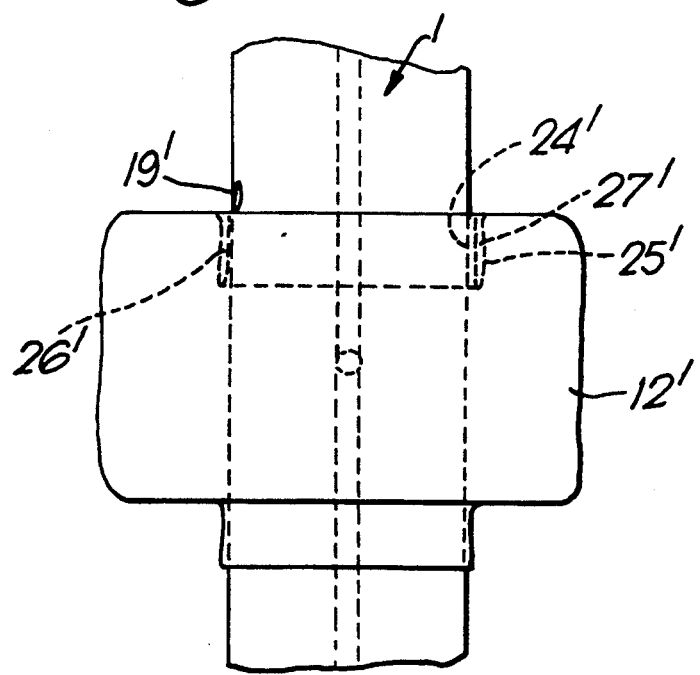
FIG. 4 is an enlarged side elevation of a part of an alternative tube.

Alternative cuff constructions are also possible in which the inflatable portion of the cuff is folded back to overlie the collar, so that the collar does not extend beyond the inflatable portion. For example, with reference to FIG. 4, there is shown a cuff 12' in which the proximal end collar 24' has its inside surface bonded to the tube, the wall of the cuff being folded back over the collar to extend in a proximal direction and then being folded back in the opposite direction. This results in an annular space 26' between the collar 24' and cuff 12' which is closed, such as by an adhesive 27', to prevent entry of secretions.

What I claim is:

1. In a medico-surgical tube of the kind comprising a tube having a bore extending therethrough that opens at both ends of the tube, a sealing cuff embracing the tube with an inflatable portion of the cuff adapted to seal the outside of the tube with the wall of a body cavity within which the tube is inserted, the sealing cuff being attached to the tube by respective proximal and distal collar portions at opposite ends of the cuff, a suction lumen extending along the tube to the region of the proximal end of the cuff, and a suction aperture opening from the lumen to the exterior of the tube adjacent the proximal end of the sealing cuff, the improvement wherein said proximal collar portion is formed by folding back the material of said sealing cuff, at the proximal end of the sealing cuff, towards said distal collar portion and along said tube inside the inflatable portion of the sealing cuff so that the inflatable portion of the sealing cuff overlies the proximal collar portion and so that the proximal end of said folded back cuff material does not extend beyond the proximal end of the inflatable portion of the sealing cuff, said suction aperture opening being located such that the bottom of said opening is at substantially the same level as the uppermost extent of said inflatable portion of the sealing cuff to permit secretions collecting in this region to be aspirated through said suction lumen.

2. A medico-surgical tube according to claim 1, wherein the suction lumen extends along the tube within the wall thickness of the tube.

3. A medico-surgical tube according to claim 1, wherein the external surface of the proximal collar portion is attached to the tube.

4. A medico-surgical tube according to claim 1, wherein the internal surface of the distal collar portion is attached to the tube.

* * * * *